(12) United States Patent
Ceragioli et al.

(10) Patent No.: US 9,926,257 B2
(45) Date of Patent: Mar. 27, 2018

(54) CONTINUOUS PROCESS FOR THE PREPARATION OF (S)-2-ACETYLOXYPROPIONIC ACID CHLORIDE

(71) Applicant: BRACCO IMAGING S.P.A., Milan (IT)

(72) Inventors: Silvia Ceragioli, Milan (IT); Pietro Delogu, Trieste (IT); Armando Mortillaro, Borgofranco d'Ivrea (IT); Alfonso Nardelli, Udine (IT); Stefano Sguassero, Udine (IT); Rosario Velardi, Udine (IT); Carlo Felice Viscardi, Milan (IT)

(73) Assignee: BRACCO IMAGING S.P.A., Milan (IT)

(*) Notice: Subject to any disclaimer, the term of this patent is extended or adjusted under 35 U.S.C. 154(b) by 0 days.

(21) Appl. No.: 14/650,868

(22) PCT Filed: Dec. 4, 2013

(86) PCT No.: PCT/EP2013/075489
§ 371 (c)(1),
(2) Date: Jun. 9, 2015

(87) PCT Pub. No.: WO2014/090650
PCT Pub. Date: Jun. 19, 2014

(65) Prior Publication Data
US 2015/0329464 A1   Nov. 19, 2015

(30) Foreign Application Priority Data
Dec. 11, 2012   (IT) .............. MI2012A2108

(51) Int. Cl.
*C07C 67/313* (2006.01)
*C07C 71/00* (2006.01)
*C07C 67/08* (2006.01)
*C07C 67/287* (2006.01)

(52) U.S. Cl.
CPC ............ *C07C 67/313* (2013.01); *C07C 67/08* (2013.01); *C07C 67/287* (2013.01); *C07C 71/00* (2013.01); *Y02P 20/582* (2015.11)

(58) Field of Classification Search
CPC ....... C07C 69/14; C07C 67/08; C07C 67/287; C07C 67/313; C07C 71/00; C07C 51/58; C07C 51/60; Y02P 20/582
(Continued)

(56) References Cited

U.S. PATENT DOCUMENTS 2,399,595 A    4/1946   Filachione et al.
2,410,740 A *  11/1946  Jones .................. C07C 69/68
                                                   560/179
(Continued)

FOREIGN PATENT DOCUMENTS

EP    0299484 A1    1/1989
EP    0 773 925 B1  5/1997
(Continued)

OTHER PUBLICATIONS

Amberlyst 15 (specification sheet, p. 1-4, obtained Apr. 18, 2016).*
(Continued)

*Primary Examiner* — Jafar Parsa
*Assistant Examiner* — Amy C Bonaparte
(74) *Attorney, Agent, or Firm* — Vivicar Law, PLLC

(57) ABSTRACT

The present invention relates to a continuous method for the preparation of (S)-2-acetyloxypropionic acid from an aqueous solution of lactic acid and acetic anhydride, in acetic acid. (S)-2-acetyloxypropionic acid is used for the preparation of (S)-2-acetyloxypropionic acid chloride, an essential intermediate compound for the preparation of Iopamidol and has to be industrially produced with high purity and suitable quality for producing Iopamidol according to the Pharmacopoeia requirements. The continuous process according to (Continued)

the invention, comprises therefore also the chlorination steps of (S)-2-acetyloxypropionic acid with thionyl chloride to give the corresponding (S)-2-acetyloxypropionic acid chloride which is further distilled to give the suitable purity characteristics for its use for the preparation of non-ionic iodinated contrast agents as Iopamidol.

24 Claims, 5 Drawing Sheets

(58) Field of Classification Search
USPC .................................................. 560/190, 231
See application file for complete search history.

(56) References Cited

U.S. PATENT DOCUMENTS

| | | | |
|---|---|---|---|
| 3,219,551 | A | 11/1965 | Carel et al. |
| 5,362,905 | A | 11/1994 | Villa et al. |
| 5,672,753 | A | 9/1997 | Drauz et al. |
| 7,667,068 | B2 | 2/2010 | Miller et al. |
| 2004/0110974 | A1 | 6/2004 | Lilga et al. |
| 2011/0251420 | A1 | 10/2011 | Disteldorf et al. |
| 2013/0150619 | A1* | 6/2013 | Miller .................... C07C 67/08 560/266 |

FOREIGN PATENT DOCUMENTS

| | | |
|---|---|---|
| EP | 1013632 A1 | 6/2000 |
| EP | 2 230 227 A1 | 9/2010 |
| GB | 1 472 050 | 4/1977 |
| JP | H06329587 A | 11/1994 |
| WO | 96/016927 A1 | 6/1996 |
| WO | 96/036590 A1 | 11/1996 |
| WO | 96/037458 A1 | 11/1996 |
| WO | 96/037459 A1 | 11/1996 |
| WO | 96/037460 A1 | 11/1996 |
| WO | 97/047590 A2 | 12/1997 |
| WO | 98/024757 A1 | 6/1998 |
| WO | 98/028259 A1 | 7/1998 |
| WO | 99/058494 A2 | 11/1999 |
| WO | 2002079142 A1 | 10/2002 |
| WO | 2012-155676 A1 | 11/2012 |

OTHER PUBLICATIONS

NIST ("Acetic Anhydride" entry, downloaded from http://webbook.nist.gov/cgi/cbook.cgi?ID=C108247&Mask=8 on Jul. 24, 2017, p. 1-6).*

Hulst, Ron, et al., "The rational design and application of new chiral phosphonates for the enantiomeric excess determination of unprotected amino acids. Remarkable pH dependency of the diastereomeric shift differences," Tetrahedron, vol. 50, No. 40, 1994, pp. 11721-11728, XP002710428.

Buisson, Didier et al., "Preparation and use of (S)-0-acetyllactyl chloride (Mosandl's reagent) as a chiral derivatizing agent," Tetrahedron Asymmetry, vol. 10, No. 15, 1999, pp. 2997-3002, XP004179155, ISSN: 0957-4166, DOI:10.1016/S0957-4166(99)00285-2.

PCT International Search Report and Written Opinion for PCT/EP2013/075489, dated Feb. 7, 2014.

O'Neil et al. (eds.), Merck Index, XIII Ed., 2001, No. 5073, p. 909, Merck & Co., Inc., Whitehouse Station, NJ.

Zhang J. et al., "Studies on the Synthesis of Iopamidol," Fine and Speciality Chemicals, 2011, 6:26-29.

Testa E. et al., "Zur Chemie der 3,3-Disubstituierten Azetidine, III," Justus Liebigs Annalen Der Chemie, 1962, 660:135-143.

Office Action for Israel application No. 239328, dated Apr. 20, 2016 (English Translation).

Office Action for Chinese application No. 201380065023.4, dated May 4, 2016 (English Translation).

Office Action for Korean application No. 10-2015-7017544, dated Apr. 20, 2017 (English Translation).

European Search Report for European application No. 14171751.2, dated Nov. 27, 2014.

PCT International Search Report & Written Opinion of the International Searching Authority for PCT/EP2015/062892, dated Aug. 20, 2015.

Testa, Emilio Von et al., "Zur Chemie der 3,3-Disubstituierten Azetidine, III", Justus Liebigs Annalen Der Chemie, Verlag Chemie GMBH, Weinheim, DE, 1962, vol. 660, pp. 135-143, XP002710427.

U.S. Appl. No. 15/315,401, Fretta, Roberta et al., filed Dec. 1, 2016, with Preliminary Amendment.

Office Action for U.S. Appl. No. 15/315,401, dated Jul. 10, 2017.

Tham, M.T., "Basic Distillation Equipment and Operation," (2009).

"Iopamidol," In: European Pharmacopeia, 7th ed., Strasbourg:Council of Europe, 2010, pp. 2266-2268.

Office Action for Chinese application No. 201380065023.4, dated Jan. 20, 2017 (English Translation).

Watson, P., "Composition of Lactic Acid," Industrial and Engineering Chemistry, 32:399-401 (1940).

English translation of Office Action for Japanese application No. 2015546944, dated Sep. 5, 2017, and sections of cited references D1-D6.

Office Action for Chinese application No. 201380065023.4, dated Oct. 16, 2017 (English Translation).

* cited by examiner

CONTINUOUS PROCESS FOR THE PREPARATION OF (S)-2-ACETYLOXYPROPIONIC ACID CHLORIDE

CROSS-REFERENCE TO RELATED APPLICATIONS

This application is the national stage application of corresponding international application number PCT/EP2013/075489, filed Dec. 4, 2013, which claims priority to and the benefit of Italian application no. MI2012A002108, filed Dec. 11, 2012, all of which are hereby incorporated by reference in their entirety.

FIELD OF THE INVENTION

The present invention relates to the preparation of a key reagent in the synthesis of contrast agents for X-ray iodinated compounds.

STATE OF THE ART

Iopamidol (The Merck Index, XIII Ed., 2001, No. 5073) (N,N'-Bis[2-hydroxy-1-(hydroxymethyl)ethyl]-5-[[(2S)-2-hydroxy-1-oxopropyl]-amino]-2,4,6-triiodo-1,3-benzenedicarboxamide (see formula), is a contrast agent widely used for diagnostic investigations by X-ray.

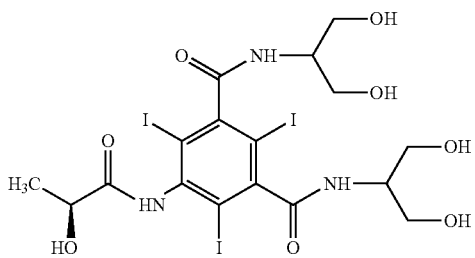 [SMILES: C[C@H](O)C(=O)Nc1c(I)c(C(=O)NC(CO)CO)c(I)c(C(=O)NC(CO)CO)c1I]

Its synthesis is known since the eighties and disclosed in GB1472050. Since then, alternative processes for its preparation have been developed, for example starting from 5-nitroisophthalic acid, suitably reduced to the corresponding amino derivative, for example by means of catalytic hydrogenation, and after that iodinated on the benzene ring so as to form the corresponding 2,4,6-triiodo derivative. This one, for example in the presence of thionyl chloride, is then converted into the corresponding dichloride of 5-amino-2,4,6-triiodoisophthalic acid (see i.e.: WO 96/037458, WO 96/037459, WO 96/016927 e WO 96/036590).

The process for Iopamidol synthesis from the dichloride of 5-amino-2,4,6-triiodoisophthalic acid (I) and its variants (see for example: WO 96/037460, U.S. Pat. No. 5,362,905, WO 97/047590, WO 98/24757, WO 98/028259 and WO 99/058494) may be schematically represented as follows:

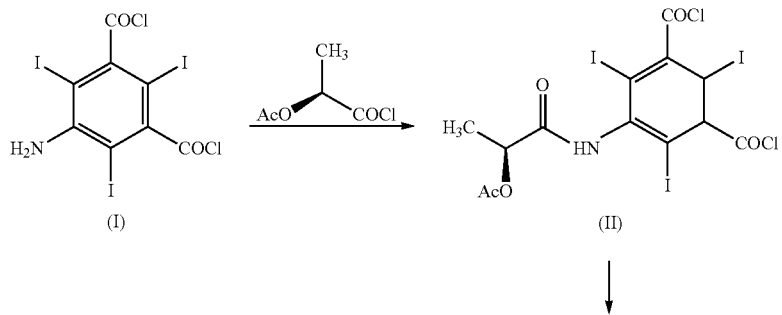

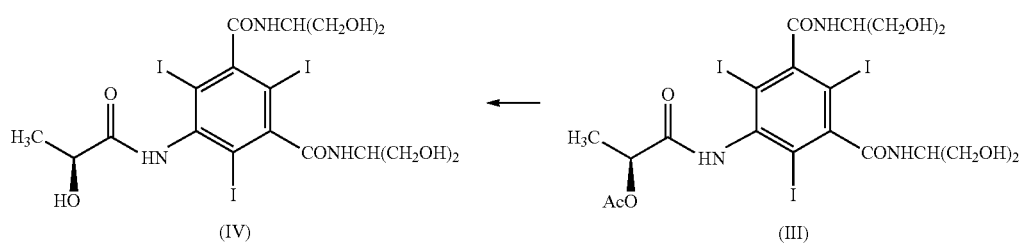

(I) is converted into the corresponding compound of formula (II) in the presence of (S)-2-acetyloxypropionic acid chloride. The so prepared intermediate compound of formula (II) is then converted into the acetyl-Iopamidol of formula (III) in the presence of 2-amino-1,3-propandiol (serinol).

At the end, the hydrolysis of the compound of formula (III) and the subsequent purification of the obtained product allow to isolate Iopamidol, compound of formula (IV) (European Pharmacopoeia 6.0 Ed. January 2008: 1115).

Even if different process variants have been disclosed and used for Iopamidol preparation, one of the key reagents, common to all the synthesis, is still the (S)-2-acetyloxypropionic acid chloride, the purity of which is crucial to achieve the Pharmacopoeia requirements on the final end product.

The preparation of this reagent is disclosed for example in EP773925, where the starting reagent is sodium lactate, in the presence of HCl and acetic anhydride, in acetic acid; the so obtained (S)-2-acetyloxypropionic acid intermediate is then chlorinated with thionyl chloride to give the corresponding chloride. Sodium lactate, commercially available but quite expensive, has to be transformed in situ, at first, into lactic acid by adding hydrochloric acid gas and then acetylated. The addition of HCl leads to the formation of sodium chloride that has to be removed by mechanical means, usually by filtration. These steps have been summarized in EP2230227 (prior art discussion).

The prior art also discloses few variants of the (S)-2-acetyloxypropionic acid synthesis and its chlorination. For example, Zhang J. et al. Fine and Specialty Chemicals, 2011, 6:26-29, discloses the preparation of (S)-2-acetyloxypropionic acid chloride starting from lactic acid, using acetyl chloride as an acetylating agent. The low yields do not allow an industrial scale development.

WO2012/155676 discloses the synthesis of (S)-2-acetyloxypropionic acid from lactic acid (85%) in toluene, in presence of acetic acid and sulfuric acid as catalyst, the reaction requires several hours at reflux.

U.S. Pat. No. 2,399,595 describes some approaches to the synthesis of (S)-2-acetyloxypropionic acid from lactic acid (pure or in 80% aqueous solutions), in the presence of acetic anhydride and acetic acid. In these approaches, reagents are used in a large excess, even when acid catalysts such as HCl or $H_2SO_4$ are employed and/or organic solvents are added to the reaction to remove water. Yields are very variable and, in any case, do not exceed 80%.

US 2004/0110974 describes the synthesis of (S)-2-acetyloxypropionic acid from 85% lactic acid in acetic acid and with $H_2SO_4$ in a continuous mode; nevertheless the absence of an acetylating agent as acetyl chloride or acetic anhydride acetylation requires high reaction temperatures that cause the formation of dimers and polymeric by-products.

Therefore, most of these approaches are carried out rather inefficiently and with a great amount of reagents waste. In fact, when water is present in the starting reagent, even in minimal amounts, the efficiency of the reaction is greatly reduced. Furthermore, in none of the prior art processes the excess reagents is recycled within the starting reactions.

SUMMARY OF THE INVENTION

The present invention relates to a continuous process for the preparation of (S)-2-acetyloxypropionic acid starting from an aqueous solution of lactic acid and performing the acetylation reaction with acetic anhydride, in acetic acid. Further, the invention comprises the chlorination of acetyloxypropionic acid and its purification to provide high quality (S)-2-acetyloxypropionic acid chloride, for use in the production of iodinated X-ray contrast agents.

Since commercial lactic acid is commonly available on industrial scale as an aqueous solution (generally sold in 50% or 88-90% concentration), water has to be distilled off and replaced by acetic acid according to phase a') of the present process, to obtain a final solution of lactic acid in acetic acid.

The final concentration of lactic acid obtained by this step is comprised from 10% to 80% by weight and is more preferably comprised from 20% to 60%.

Step a), where lactic acid in acetic acid is acetylated with acetic anhydride, provides for a (S)-2-acetyloxypropionic acid reaction mixture from which the acetic acid and the residual acetic anhydride are distilled off according to step b), to obtain (S)-2-acetyloxypropionic acid.

In the process, lactic acid acetylation is carried out preferably in the presence of an acidic catalyst, even more preferably of a heterogeneous catalyst, selected from the group consisting of: a Brønsted acid and a Lewis acid. Particularly preferred are the acidic catalysts selected from the group consisting of: a sulfonic resin in its acidic form, a zeolite and a montmorillonite.

According to a preferred embodiment, acetic acid distillation in step b) takes place in two steps.

The process is used for the preparation of (S)-2-acetyloxypropionic acid chloride and therefore comprises the continuous chlorination of 2-acetyloxypropionic acid in the presence of thionyl chloride and its distillation. Chlorination with thionyl chloride takes place in at least 2, preferably 3 distinct/independent reactors each one endowed with its own condensation unit and with its own independent condensate recirculation system to the reactor where the chlorination reaction takes place.

DETAILED DESCRIPTION OF THE INVENTION

Figure 1:
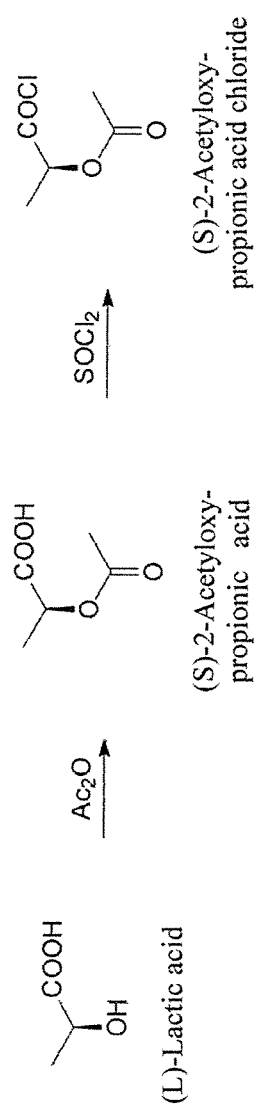
FIG. 1. Scheme of the synthesis reaction
FIG. 2. Chlorination reaction
FIG. 3. Continuous process. Scheme of the embodiment comprising steps a')-a)-b)-c)-d).

The present invention relates to a continuous process for the preparation of (S)-2-acetyloxypropionic acid starting from an aqueous solution of lactic acid and performing the acetylation reaction with acetic anhydride, in acetic acid.

On its turn (S)-2-acetyloxypropionic acid is the starting material for the preparation of (S)-2-acetyloxypropionic acid chloride, a crucial intermediate compound for Iopamidol preparation. The (S)-2-acetyloxypropionic acid chloride has to be prepared with a high purity and a suitable quality to produce Iopamidol according to the Pharmacopoeia requirements.

The continuous process according to the invention comprises the steps of:
a') replacement of water with acetic acid in the lactic acid solution, carried out by feeding a distillation column with a commercial aqueous lactic acid solution and with a stream of acetic acid, wherein water is distilled off to obtain a final solution of lactic acid in acetic acid;

a) acetylation of lactic acid, carried out in a reactor where the lactic acid in acetic acid is acetylated in presence of acetic anhydride to give (S)-2-acetyloxypropionic acid;

b) distillation of acetic acid from the solution obtained in a), comprising (S)-2-acetyloxypropionic acid in acetic acid, to provide (S)-2-acetyloxypropionic acid. This distillation removes also the excess acetic anhydride.

Acetylation of lactic acid with acetic anhydride has been formerly attempted by homogeneous catalysis, as in U.S. Pat. No. 2,399,595, where important quantities of acetylated dymers of lactic acid are formed, which lower yield and make the process not interesting from the industrial point of view. In order to avoid this problem, sodium lactate has been used as a starting reagent.

Using sodium lactate dimerisation is minimized, but relevant quantities of sodium acetate are formed. By adding HCl (see eg. EP 773925), a NaCl precipitate forms that has to be removed by mechanical means, generally by filtration and this by-product has to be disposed as a waste.

Prior art drawbacks are avoided in the present process, where the acetylation reaction is fed by lactic acid in acetic acid. On an industrial scale process, this is achieved by using lactic acid of a commercial grade (i.e. in an aqueous solution) and replacing water with $CH_3COOH$ in continuous and in situ before its use.

This avoids the use of lactic acid in aqueous solutions in the acetylation reaction a) which is not convenient, because the addition of acetic anhydride directly into the lactic acid aqueous solution would involve an excessive consumption of this reactant, thus rendering the whole process far less attractive from an industrial point of view.

It is therefore highly desirable to remove water from the commercial solution of lactic acid, available at different concentrations (for example 30%, 50% or 88-90% lactic acid solutions). As said above, in this process water is distilled off and acetic acid is introduced to obtain a final solution of lactic acid in acetic acid at a lactic acid concentration comprised from 10% to 80%, preferably 40-60% by weight, according to step a') of the process.

Preferably a commercial lactic acid solution is used (FIG. 3, [1]) at a concentration comprised from 25 to 60%, typically about 50%.

Figure 3:
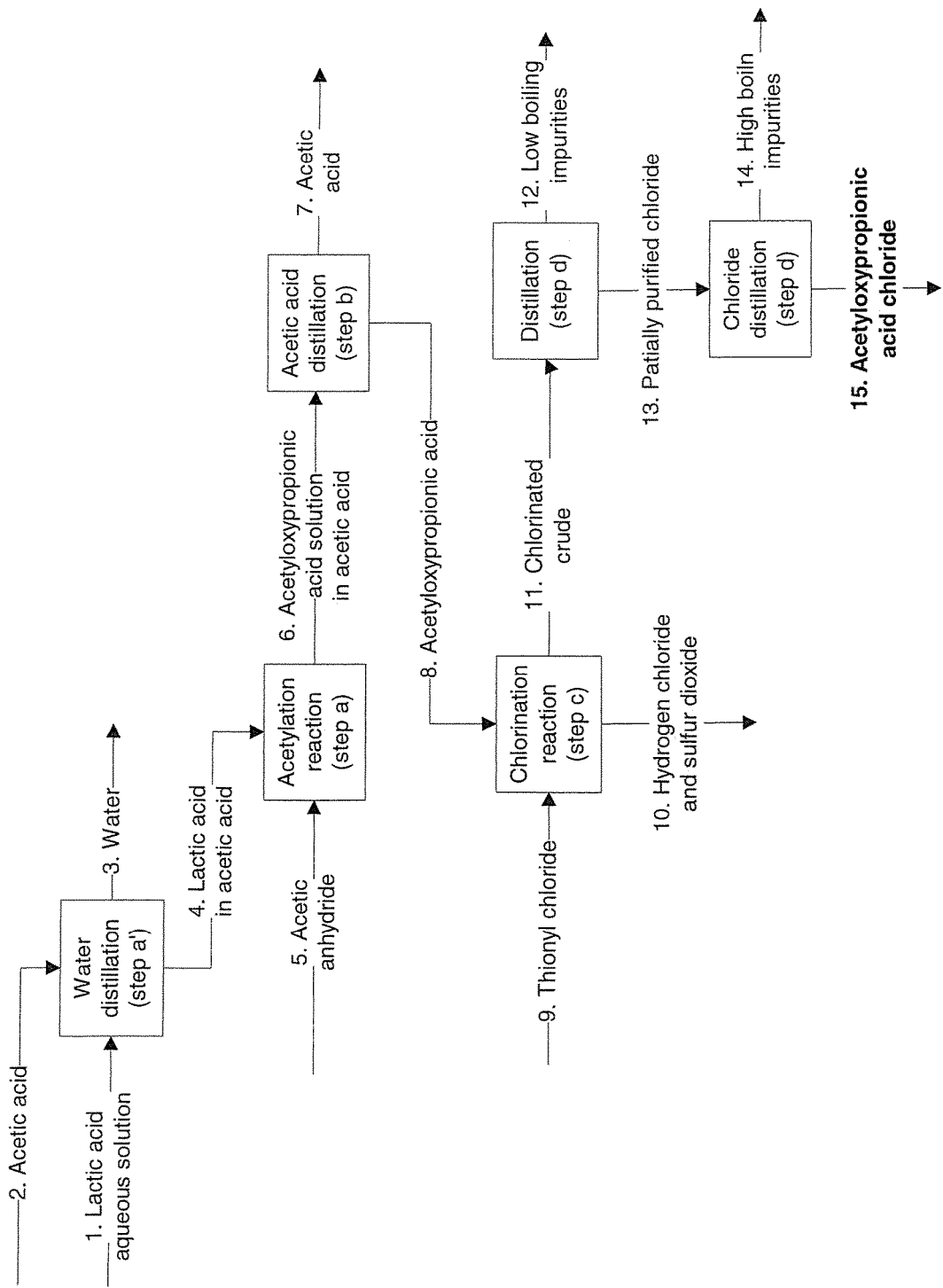

Water replacement in step a') is preferably carried out by distillation on a distillation column continuously fed with lactic acid in water solution and with an acetic acid stream from the bottom, this latter either in liquid or vapor phase (FIG. 3). Water or a mixture of water and acetic acid is removed as a column head product (FIG. 3), while lactic acid in acetic acid solution is the end product at the bottom.

The distillation column may be a column endowed with distillation plates or with packing material, preferably fed at its base with anhydrous acetic acid either in liquid or vapour phase and at its head with the lactic acid aqueous solution. A column with a plate number comprised from 8 to 30 guarantees an almost complete separation of water from lactic acid.

The distillation is preferably carried out under vacuum, at residual pressures comprised from 10 to 400 mbar, more preferably from 20 to 100 mbar.

Lower pressure values are possible, but they require the use of columns having larger diameters, and then more expensive.

The acetylation reaction in step a) is carried out by feeding the reactor with lactic acid in acetic acid solution and with acetic anhydride [5] preferably in a slight molar excess of acetic anhydride, wherein such an excess is comprised from 1 mol % and 40 mol % (1:1.01-1:1.40 lactic acid:acetic anhydride range molar ratio).

The reaction is preferably carried out at a temperature comprised from 20° C. to 120° C., even more preferably at temperature comprised from 30° C. and 60° C.

The acetylation reaction is carried out in the presence of an acid catalyst, more preferably a catalyst in the heterogeneous phase (referred also in this description as a "heterogeneous catalyst") which can be introduced and immobilized into the acetylation reactor bed, does not require additional operations for its removal and can be recycled.

By heterogeneous or solid phase catalyst is intended a catalyst in the solid phase, wherein the cation exchanging groups are bound to a solid phase, i.e. a matrix either polymeric or reticular, inert in the harsh conditions of the acetylation reaction.

Preferred acid catalysts in the heterogeneous phase are the Brønsted or the Lewis acids. In particular, among the first type, cationic resins are preferred, even more preferably sulfonic resins in the acid form, such as for example Amberlyst™ 15 Dry, which is the most preferred. Zeolites and montmorillonites belong to the second type of heterogeneous acid catalysts, such as for example Montmorillonit K10 and Nafion™, Montmorillonit NR 50. Amberlyst™ 15 Dry type resins are preferred as they are commercially available in an anhydrous form. Other strong cationic resins with a reticular type-like matrix, in their dry form may be used with comparable results.

The acetylation reactor may be selected among different types of reactors.

According to an embodiment, the reactor is a plug-flow. In the case a heterogeneous catalyst is used, it is preferably of the fixed-bed type. Inert filling materials, such as Rashig rings or glass beads, are also preferably used in this type of reactor along with the catalyst to balance catalyst volume and thermal exchange surface.

According to an alternative embodiment, the reaction is performed in a loop system, recirculating the reaction mixture on one or more beds containing the heterogeneous catalyst.

According to a preferred embodiment, the reactor is made by two in series reactors, wherein the first one is a loop reactor with recirculation on a heterogeneous catalyst bed and the second one is a plug-flow reactor with fixed resin bed, where the conversion of lactic acid into (S)-2-acetyloxypropionic acid is completed.

Reaction a) is exothermic, thus the reactor geometry has to provide an optimal thermal exchange to ensure a particularly effective temperature control, which is essential in avoiding side reactions and limiting impurities production, thus optimizing reaction yields.

In a preferred embodiment, acetylation is performed with a residence time of less 1 h, at the above indicated temperature conditions in a limited reactor size.

Namely, limiting the residence time and optimizing the heat-discharging capability during the water distillation and the acetylation reaction are both very important aspects for the industrialization of the present process.

Although apparently quite simple, the (S)-2-acetyloxypropionic acid synthesis starting from lactic acid becomes extremely complex from a practical point of view, because lactic acid has two potentially reactive functional groups. On a large scale and in order to produce (S)-2-acetyloxypropionic acid chloride of high standard quality, is critical both the preliminary removal of water (step a') and the acetylation reaction (step a). In fact, the possible concurrent lactic acid polymerization, greatly reducing the yields and giving by-products that must be cleared off, has to be avoided, since it causes an important economic and environmental burden.

In the prior art, the use of sodium lactate as a raw starting material avoided water distillation and limited by-products formation, thus making the sodium lactate synthesis suitable for an industrial use. However, as above disclosed, it was necessary to remove the sodium chloride formed as a reaction by-product. This additional operation, carried out by filtration, was in any case preferred in comparison to the disadvantages of the direct lactic acid acetylation in a batch process, using lactic acid solution comprising even small quantities of water.

It has now been found that the continuous process according to the present invention strongly reduces the drawbacks related to the use of aqueous solutions of lactic acid for the preparation of (S)-2-acetyloxypropionic acid. In fact, advantageously, in the continuous process of the present invention, the minimization of the lactic acid residence time in the distillation reboiler as well as of the next reactions times, greatly reduces oligomers formation thus allowing to obtain almost quantitative yields. This makes the use of lactic acid as a starting reagent in the acetylation reaction industrially feasible.

In particular step a') in continuous offers the following advantages in comparison to a batch process:
 a higher efficiency in the separation between water and acetic acid and the consequent reduction of the refluents;
 the obtainment of a lactic acid in acetic acid solution with controlled water amounts, preferably less than 3% even more preferably less than 1%, with the consequent reduction of acetic anhydride consumption during the subsequent acetylation reaction;
 a short lactic acid residence time in the reboiler (less than 30' and preferably around 15 min), which minimizes oligomers formation;
 due to the short residence times, the possibility to use higher distillation temperatures and lower vacuum conditions in comparison with what is needed in batch, with a sensible decrease in the column size.

Furthermore, the use of lactic acid is advantageous over sodium lactate for the following reasons:
i) the commercial reagent is quite cheaper than sodium lactate;
ii) it is avoided, as already discussed above, sodium chloride formation, to be taken away from the reaction by mechanical means.

Advantageously, the present process provides for the same purity grade of the final product achieved with former industrial methods and suitable, for Iopamidol production under the presently in force European Pharmacopoeia.

Moreover, the continuous process provides further advantages e.g. the possibility to recirculate and/or reuse at least some of the reagents. In particular, according to one of the preferred embodiments disclosed in FIG. 5, in step a') where water distillation/replacement takes place, the vapor or liquid acetic acid feeding ([II]) preferably comes from the acetic acid distillation carried out in step b), after the lactic acid acetylation, rather than with freshly purchased acetic acid. As already mentioned, lactic acid acetylation with acetic anhydride, is carried out in an acetic acid solution and gives acetic acid as by-product, offering the possibility to recover said by-product after distillation in b) for recirculation in a').

In the presence of an acid catalyst in the heterogeneous phase in step a) corresponding to the preferred embodiment, the reaction is fast, with conversion times below 30 min. The reaction takes place also in the absence of a catalyst, but at higher temperatures and in longer times (for example at 70-100° C. h for more than 2 h) while the addition of an acid catalyst allows to complete the reaction in less than 30 min, preferably in about 25 min, operating at temperatures considerably lower (30-60° C., more preferably 35-55° C.). As said above, a homogeneous acid catalysts can also be used in this reaction. Among useful catalysts, strong acids such as sulfuric acid and perchloric acid should be mentioned; these, however have to be necessarily removed before the distillation step. Therefore, although this represents a workable embodiment, it is far less advantageous than the former because of the additional steps (i.e. a neutralization and further salts removal by i.e. filtration) to be provided for.

Figure 4:
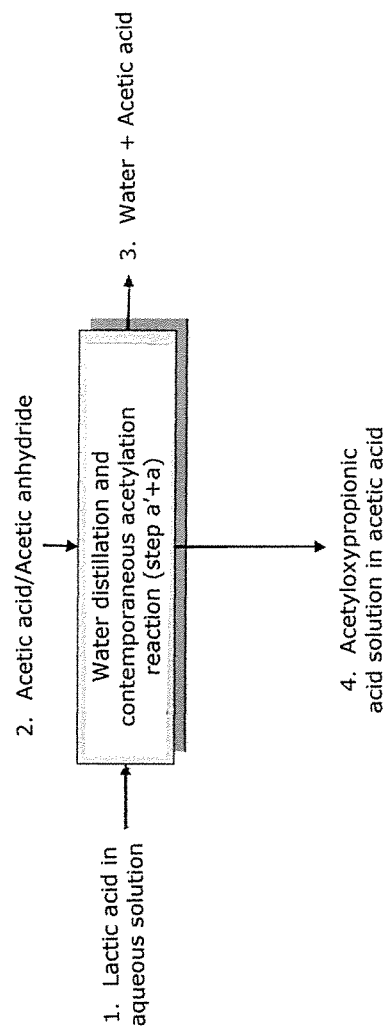
FIG. 4. Continuous process. Scheme of the embodiment with water distillation and acetylation carried out in the same reactor.

The acetylation reaction a) can also be carried out according to an alternative embodiment, shown in FIG. 4, i.e. directly during water distillation a').

This is achieved by feeding the distillation column with the commercial lactic acid aqueous solution and the reboiler with an acetic anhydride stream or with a mixture of acetic acid and acetic anhydride at the bottom [2]. In this case the preferred molar ratio between acetic anhydride and lactic acid is comprised from 1.01:1 to 1.4:1. The acetic anhydride flux may comprise acetic acid as a solvent, in a weight ratio with acetic anhydride comprised from 0.2:1 to 5:1.

According to this embodiment, the (S)-2-acetyloxypropionic acid in acetic acid (FIG. 4) is directly produced inside the distillation reboiler. The advantage of this alternative is the possibility to use a single apparatus for both removing water and acetylating the lactic acid, exploiting the exothermic heat produced by the acetylation reaction to evaporate water.

Figure 5:
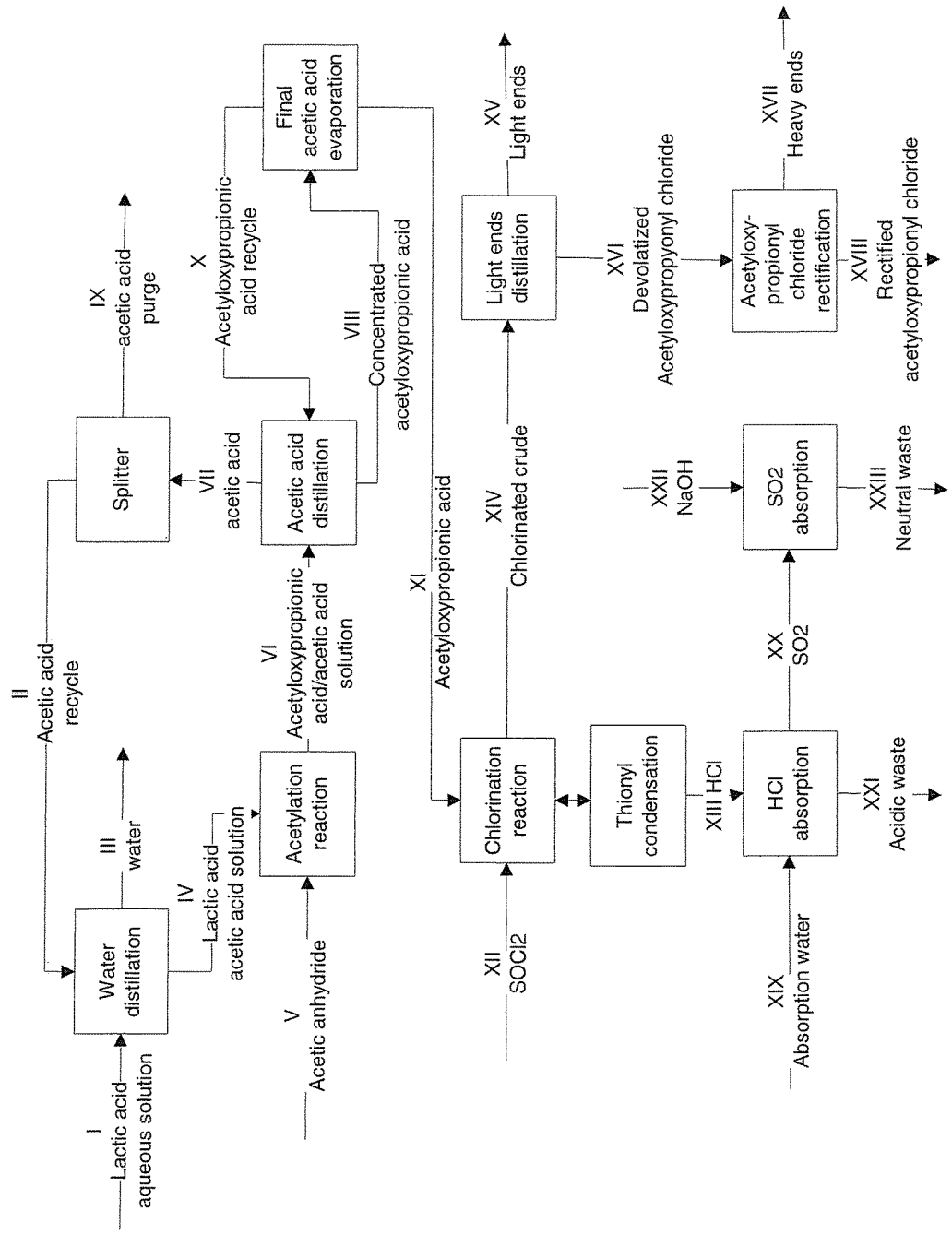
FIG. 5. Continuous process. Scheme of the embodiment with the indication of the preferred recyclings.

The solution of (S)-2-acetyloxypropionic acid in acetic acid, obtained according to each of the alternative embodiments of the acetylation reactions, is distilled according to step b) to remove the acetic acid and the residual acetic anhydride which are preferably recycled in step a'), and providing the product (S)-2-acetyloxypropionic acid (FIG. 3: [8]; FIG. 5: XI) at the bottom of the column, for the next chlorination reaction.

Acetic acid and acetic anhydride distillation in step b) avoids the generation of the by-product acetyl chloride in the subsequent chlorination reaction, with thionyl chloride consumption and, most importantly, with formation of acidic by-products which have to be removed during the end product purification.

According to the preferred embodiment schematized in FIG. 5, distillation is carried out in two subsequent steps: firstly, the effluent from the acetylation reactor ([VI], also represented in FIG. 3 with [6] or in FIG. 4 with [4]) is directed to a first distillation column under vacuum, at pressure values lower than 100 mbar. In this column, acetic acid and acetic anhydride are removed by distillation, while a concentrated solution of (S)-2-acetyloxypropionic acid is obtained at the bottom; such a concentrated solution may still comprise some acetic acid and acetic anhydride. Accordingly, a further distillation step (FIG. 5 final evaporation) is preferably carried out to reduce further acetic acid and acetic anhydride.

According to this embodiment the first distillation step is carried out, for example on a distillation column, operating at temperatures comprised from 70 to 90° C. (usually 80° C., 20 mbar) until a residual acetic acid content below 15%, preferably below 10% in (S)-2-acetyloxypropionic acid, is obtained.

The second distillation step is carried out, e.g., in a stirred reactor or in thin-film evaporator operating at higher temperatures, for example comprised from 100 to 130° C. and at pressure values below 30 mbar (preferably 120° C., 20 mbar), thus obtaining a residual acetic acid content below 3%, preferably below 2%. Vapors obtained in the second distillation step may be recycled to the first step to recover (S)-2-acetyloxypropionic acid contained in the distillate.

However, acetic acid distillation may also be carried out continuously in a single step, as disclosed e.g. in FIG. 3, by using a column equipped with a suitable reboiler with a low residence time, for example an evaporator of the falling-film type.

As disclosed above, it's possible to recover and recycle the acetic acid and acetic anhydride (FIG. 5 [X]) obtained from the final evaporation of acetic acid, either in liquid or vapor phase, to feed the column in the first step (a'), i.e. to replace water of the lactic acid aqueous solution with acetic acid.

Carrying out such a recycling procedure represents therefore a preferred embodiment of the continuous process, steps a')-a)-b) as depicted in FIG. 5, steps from VI to XI.

The (S)-2-acetyloxypropionic acid, devoid of acetic acid and acetic anhydride removed by distillation in phase b), then undergoes to:

c) chlorination with thionyl chloride to give the corresponding chloride;
d) purification, preferably by distillation, of the (S)-2-acetyloxypropionic acid chloride.

Therefore the continuous process comprises preferably steps: a'), a), b), c), d) and is suitable for the industrial production of high purity (S)-2-acetyloxypropionic acid chloride to be used in the synthesis of iodinated contrast agents, in particular Iopamidol.

According to a preferred embodiment, the chlorination reaction c) is carried out in a reactor comprising a series of at least 2 CSTR reactors (Continuous Stirred-Tank Reactor), wherein each element is equipped with its own condensation unit and its own independent gas outlet allowing to recycle the thionyl chloride condensed in each unit back into the starting reactor, thus ensuring a suitable thionyl chloride concentration in every section of the plant.

According to particularly preferred embodiments, in step c) the conversion of (S)-2-acetyloxypropionic acid is higher than 80%, preferably higher than 90%, even more preferably higher than 95% with a residence time not higher than 3 hours. This is achieved by the use of chlorination reactors in a series of 2 and even more preferably of at least 3, or 4, or 5, or 6 CSTRs, each one endowed with its own condensation unit and its own independent gas outlet and with $SOCl_2$ recycling into the starting chlorination reactor.

The chlorination reaction c) also produces hydrochloric acid and sulfurous anhydride ($SO_2$ and HCl, see FIG. 2) as by-products that leave the reactor under the gas form (FIG. 3). Also thionyl chloride produces vapours, recovered, as disclosed above, by one or more condensation units. Actually, while hydrochloric acid and sulfurous anhydride are to be disposed off, thionyl chloride, is recovered, re-condensed and recycled into the starting element (FIG. 5, thionyl condensation).

In a preferred embodiment the acidic gases coming from the chlorination reactor and from the next distillation column are treated before their emission to cut down hydrochloric acid, sulfurous anhydride, acetyl chloride and possible traces of thionyl chloride, as shown in FIG. 5, steps XIII, XXI, XXIII, according to the local law requirements.

According to this aspect, the chlorination reaction of (S)-2-acetyloxypropionic acid in continuous, in particular by the CSTRs cascade, is particularly advantageous in comparison to the batch process for at least two reasons: the production of the acidic gases occurs at a constant flow rate thus allowing the cutting-down system to work under stationary conditions with a clear advantage for the process safety; furthermore, thionyl chloride, which is also extremely dangerous, is recovered and recycled without significant dispersion or loss (FIG. 5, condensation).

The final product (S)-2-acetyloxypropionic acid chloride is isolated from the mixture deriving from the end of the chlorination reaction c) (FIG. 3 and FIG. 5 XIV) and purified, preferably by distillation (step d), carried out in two steps. Accordingly, the low-boiling impurities [12] are removed first, then the high-boiling ones [14], like the residual 2-acetyloxypropionic acid and the oligomers of the (S)-2-acetyloxypropionic acid chloride (in FIG. 5 steps XV and XVII).

The product obtained after the second distillation has the following specifications:

| | |
|---|---|
| (S)-2-acetyloxypropionic acid chloride | 98.0-102.0% |
| Thionyl chloride | ≤1.0% |
| Acetyl chloride | ≤0.2% |
| Lactyl chloride/others | ≤2.0% | and is thus suitable for the synthesis of iodinated contrast agents for diagnostic use in vivo, according to the requirements of the European Pharmacopoeia presently in force.

A continuous reaction cycle, carried out on an industrial plant (production>80 kg/h, preferably >100 kg/h, up to 500 kg/h) according to the present invention, steps a')-d), has typically an overall yield higher than 90% and is therefore suitable for a large scale production.

The Experimental Part and the drawings are intended to integrate the present description, without representing limitations of it.

In particular in FIG. 1 are schematized the reactions according to steps a)-c).

Figure 2:
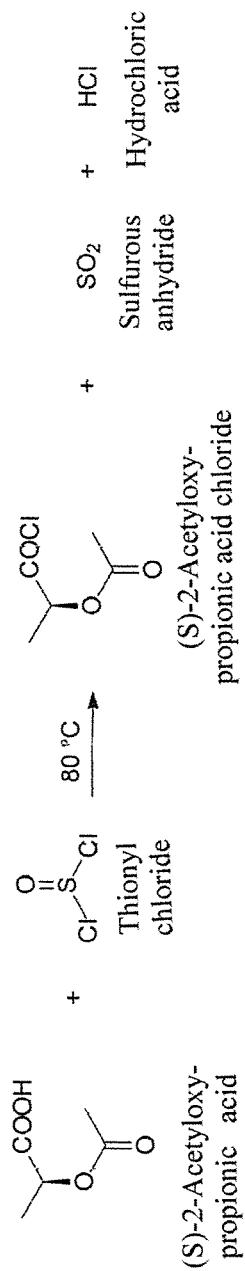

In FIG. 2 are disclosed the co-products (sulfurous anhydride, $SO_2$, and hydrochloric acid, HCl) which are formed during the reaction with thionyl chloride ($SOCl_2$).

The diagram schematic of the whole process, comprising steps a')-d), which leads to (S)-2-acetyloxypropionic acid chloride in purified form and suitable for the preparation of Iopamidol, is shown in FIG. 3, where is described the realization of the continuous process according to steps a')-d).

FIGS. 4 and 5 describe some of the preferred embodiments: in particular, FIG. 4 shows the above disclosed process variant, in which acetylation is carried out during water distillation in step a').

In FIG. 5, the diagram schematic shows also the preferred recyclings. The streams, optionally recirculated, have been indicated with roman types number according to an exemplary preferred embodiment; this figure does not represent the alternative embodiment of FIG. 4, which can however be used.

EXPERIMENTAL SECTION

Example 1. Preparation of Lactic Acid in Acetic Acid

A commercial solution of lactic acid in water, containing 46.5% lactic acid monomer and 3.2% dimer, was fed to the first plate, starting the count form the head, of an Oldershaw distillation column having the diameter of 5 cm, equipped with 30 perforated plates, at the bottom of which a stream of acetic acid was fed. The flow rates of the two feedings were, respectively, of 1040 and 550 mL/h. The column head pressure was 50 Torr and the reflux ratio 1.

The distillate flow rate was 550 mL/h. The head product contained only water and traces of acetic acid, while the composition (% weight) of the product from the bottom of the column was the following:

TABLE 1

| Component | % weight |
|---|---|
| Lactic acid | 40.0 |
| Lactic acid dimer | 3.9 |
| (S)-2-acetyloxypropionic acid | 0.5 |
| (S)-2-acetyloxypropionic dimer | 0.3 |
| Water | 2.8 |
| Acetic acid | 51.6 |

Example 2. Acetylation of Lactic Acid a. Homogeneous Catalysis

A lactic acid solution in acetic acid, containing 51.1% of lactic acid and 5.9% of oligomers with a ratio oligomers/lactic acid equal to 0.11 was fed into a tubular reactor having a volume of 2.6 L, with a diameter of 2 cm. The reactor was equipped with a thermostatic jacket. The fluid temperature inside the reactor was kept at 57° C. The solution was fed into the reactor together with a stream of acetic anhydride containing sulfuric acid, at a flow rate such that the molar ratio between acetic anhydride and lactic acid was of 1.3/1. The sulfuric acid concentration in the reaction mixture was of 0.5% by weight. The residence time inside the reactor was 89 min and the % conversion obtained shown in Table 2. The effluent from the reactor was continuously directed into an evaporator, working at 8 mbar, having a reboiler volume of 2 L, in which most of the acetic acid was removed by distillation. The reboiler temperature was 95° C.

The streams compositions at the exit of the acetylation reactor and at the evaporator (bottom) were respectively the following:

TABLE 2

| | Reactor exit (% weight) | Evaporator exit (% weight) |
|---|---|---|
| Lactic acid | 1.06 | 0.36 |
| Acetic acid | 46.8 | 5.8 |
| (S)-2-acetyloxypropionic acid | 43.6 | 59.1 |
| (S)-2-acetyloxypropionic dimer | 7.3 | 21.3 |

Thus, the ratio of acetylated oligomers/acetyloxypropionic acid at the exit of the acetylation reactor was 0.17, while was increased to 0.38 at the evaporator exit.

b. Heterogeneous Catalysis

A lactic acid solution in acetic acid, containing 56.4% of lactic acid and 6% of oligomers, with a ratio oligomers/lactic acid equal to 0.11, was fed into a tubular reactor having a 4 cm diameter containing 60 g of Amberlist® 15, a sulfonic resin in its acid form with 4.7 meq/g of sulfonic groups. The reactor was equipped with a thermostatic jacket. The solution was fed into the reactor together with a stream of acetic anhydride, at a flow rate such that the molar ratio between acetic anhydride and lactic acid was of 1.38/1. The spatial speed was of 29.8 (g/h)/g of resin in the reactor.

The fluid temperature in the reactor was 47° C.

The effluent from the reactor was continuously sent to an evaporator, working at 10 mbar, having a 2 L boiler volume, which separated most of the acetic acid. The boiler temperature was 84° C. Acetic acid and the residual acetic anhydride were removed with the distillate at the evaporator head, while (S)-2-acetyloxypropionic acid and the heavy compounds were collected at the exit of the reboiler.

The percent compositions of the streams at the exit of the acetylation reactor and of the evaporator (bottom) were the following:

TABLE 3

| Component | Reactor exit (% weight) | Evaporator exit (% weight) |
|---|---|---|
| Lactic acid | 0.6 | 0 |
| Acetic acid | 42.6 | 7 |
| Lactic acid dimer | 1.3 | 0.15 |
| (S)-2-acetyloxypropionic acid | 51.6 | 85.7 |
| Lactic acid trimer | 0 | 0.08 |
| Acetylated dimer | 3.7 | 6.8 |
| Acetylated trimer | 0.16 | 0.3 |

Thus the ratio of acetylated oligomers/acetyloxypropionic acid was comparable at the exit of the acetylation reactor and at the exit of the evaporator (bottom), being respectively 0.10 and 0.09.

The comparison between the results of Example 2a and Example 2b shows that the presence of a homogeneous catalyst which is not removed at the end of the reaction, caused a certain dimerization of (S)-2-acetyloxypropionic acid in the evaporator reboiler. Alternatively, with the heterogeneous catalyst which is maintained inside the acetylation reactor, the mixture at the exit of the reactor is devoid of the catalyst and is stable even at relatively high temperatures, such as those adopted in the evaporator. Hence by using a heterogeneous catalyst, (S)-2-acetyloxypropionic acid can be obtained with a quantitative yield, considering the sum of the acetylation and the subsequent distillation step.

Example 3. Chlorination of Acetyloxypropionic Acid 3.1. Preparation with 3 Reactors and One Condensation Unit.

(S)-2-Acetyloxypropionic acid obtained from the bottom of the evaporator described in Example 1 was fed together with thionyl chloride into a series of reactors formed by a continuous stirred reactor endowed with a reflux condensation unit and by two horizontal tubular reactors (PFR1 and PFR2) in series, which reaction gases were directed to the condensation unit of the first stirred reactor. The condensate from each condensation unit was completely re-directed to the first stirred reactor. The useful volumes of the 3 reactors were respectively 586, 1380 and 1480 mL, amounting to a total volume of 3446 mL.

The acetyloxypropionic acid solution contained, apart from the acid itself, 2% by weight of acetic acid, 6% by weight of acetylated dimer and around 2% of other products. The feeding flow rate of the solution to the first reactor was of 524.7 g/h, corresponding to a flow rate of acetyloxypropionic acid of 522.8 g/h. Into the first reactor was also fed thionyl chloride at a flow rate of 522.8 g/h. The feeding molar ratio between thionyl chloride and acetyloxypropionic acid resulted to be of 1.24 moles/mole, while the ratio between thionyl chloride and the sum of all the reactive carboxylic groups was of 1.14 moles/mole.

With reference to the inlet conditions, taking into account the thionyl chloride density, the overall permanence time resulted to be of 4.1 hours.

Once reached the steady state, the temperatures of the three reactors were equal to, respectively, 76.4° C., 76.7° C. and 71.9° C.

The residual concentrations of the two reagents at the exit from each reactor were measured, obtaining the following results:

TABLE 4

| position | Residual (S)-2-acetyloxypropionic acid | $SOCl_2$ |
|---|---|---|
| CSTR | 21.01% | 26.7% |
| PFR 1 | 18.10% | 14.5% |
| PFR 2 | 12.70% | 7.7% |

Thus, it is worth noting that with a single condensation unit and a permanence time of 4 hours conversion is not completed.

3.2. Preparation with 3 Reactors with Distinct Condensation Units.

(S)-2-Acetyloxypropionic acid was fed together with thionyl chloride into a series of 3 stirred continuous reactors each one endowed with its own reflux condensation unity. The condensate from each condensation unity was completely sent again to the starting stirred reactor. The useful volumes of the 3 reactors were respectively of 40, 38 and 44 mL, amounting to a total volume of 122 mL.

The titer of the (S)-2-acetyloxypropionic acid solution was 98% in this experiment. The feeding flow rate of the solution into the first reactor was 30.4 g/h. Thionyl chloride was fed into the first reactor at a flow rate of 28.7 g/h. The feeding molar ratio between thionyl chloride and acetyloxypropionic acid was 1.05 moles/mole.

With reference to the inlet conditions, taking into account the thionyl chloride density, the overall permanence time was 4.0 hours.

Once reached the steady state, the temperatures of the three reactors were respectively: 85, 88 and 85° C.

The compositions at the exit from each reactor were measured, obtaining the following results:

TABLE 5

| Exit | Residual (S)-2-acetyloxypropionic acid | $SOCl_2$ |
|---|---|---|
| R1 | 3.4% | 12.4% |
| R2 | 1.8% | 6.5% |
| R3 | 0.8% | 5.5% |

Thus, with this reactor set up, by using a permanence time of 4 hours, the same as in Example 3.1, the (S)-2-acetyloxypropionic acid conversion (the residue measured by HPLC) was almost complete.

3.3. Preparation with 6 Reactors with Distinct Condensation Unities.

(S)-2-acetyloxypropionic acid was fed together with thionyl chloride into a series of 6 continuous reactors of about the same volume, each one endowed with its own reflux condensation unity. The condensate from each condensation unity was completely sent again to the starting stirred reactor. The total volume of the 6 reactors was of 4389 mL.

The titer of the (S)-2-acetyloxypropionic acid solution was 92%. The feeding flow rate of the solution into the first reactor was of 839 g/h. Into the first reactor was also fed thionyl chloride at a flow rate of 998 g/h. The feeding molar ratio between thionyl chloride and acetyloxypropionic acid was 1.26 moles/mole.

With reference to the inlet conditions, taking into account the thionyl chloride density, the overall permanence time was 3.03 hours.

Once reached the steady state, the temperature of the first reactor was 59° C., the one of the second 66° C. and the one of the fourth 74° C.

The compositions at the exit from each reactor were measured, obtaining the following results:

TABLE 6

| | % acetyl chloride | % (S)-2-acetyl-oxypropionic acid chloride | % acetylated dimer | % $SOCl_2$ | % residual acetyl-oxypropionic acid |
|---|---|---|---|---|---|
| Reactor 1 | 4.05 | 74.08 | 0.72 | 11.10 | 10.05 |
| Reactor 2 | 3.60 | 83.30 | 0.97 | 7.60 | 4.53 |
| Reactor 3 | 3.20 | 85.14 | 1.01 | 6.30 | 4.35 |
| Reactor 4 | 3.20 | 88.92 | 1.03 | 5.40 | 1.45 |
| Reactor 5 | 3.10 | 89.14 | 0.98 | 4.60 | 2.18 |
| Reactor 6 | 3.08 | 90.45 | 1.06 | 3.60 | 1.81 |

These results demonstrate that, with a number of reactors in series equal to 6 the almost complete conversion of (S)-2-acetyloxypropionic acid is obtained with a permanence time of 3 hours only.

Example 4. Rectification of Raw
(S)-2-Acetyloxy-Propionyl-Chloride

The raw chlorination product obtained in preparation 3.1 was directed to the 13$^{th}$ plate of a first continuous distillation Oldershaw column having a diameter of 1 inch, carrying 25 perforated plates, working at an head pressure of 30 Torr, in which the head light products, acetyl chloride and thionyl chloride, were removed obtaining from the reboiler a (S)-2-acetyloxypropionylchloride devoid of volatile products. The product from the reboiler itself was fed to the 20$^{th}$ plate starting from the head of a second continuous distillation column having a diameter of 1 inch, carrying 25 perforated plates, head-separating a product with a titer of 99. %.

The invention claimed is:

1. A continuous process for the preparation of (S)-2-acetyloxypropionic acid starting from a commercial grade aqueous (L)-lactic acid solution comprising the following steps:
   a') replacing water with acetic acid in said aqueous (L)-lactic acid solution by distilling off water from the aqueous (L)-lactic acid solution while simultaneously introducing an acetic acid stream, wherein said stream is either in a liquid or in a vapour phase, to get a final solution of (L)-lactic acid in acetic acid, wherein the water is almost completely separated from the final solution,
   a) carrying out an acetylation of said (L)-lactic acid in said acetic acid with acetic anhydride to give (S)-2-acetyloxypropionic acid in acetic acid in the presence of a heterogeneous acid catalyst, and
   b) recovering the (S)-2-acetyloxypropionic acid by distilling off acetic acid and excess anhydride from (S)-2-acetyloxypropionic acid.

2. The process according to claim 1, wherein the heterogeneous acid catalyst is selected from the group consisting of: a sulfonic acid resin, a zeolite and a montmorillonite.

3. The process according to claim 1, wherein the acetylation of step a) is carried out in a distillation column.

4. The process according to claim 1, wherein step a') is carried out in a distillation column and wherein the acetic acid distilled off in step b) is recycled to the acetic acid stream entering the distillation column.

5. The process according to claim 1, wherein the distillation of the acetic acid from the (S)-2-acetyloxypropionic acid in acetic acid is carried out in two steps.

6. A process for the preparation of (S)-2-acetyloxypropionyl chloride starting from a commercial grade aqueous (L)-lactic acid solution comprising the following steps:
   a') replacing water with acetic acid in said aqueous (L)-lactic acid solution by distilling water from the aqueous (L)-lactic acid solution while simultaneously introducing an acetic acid stream, wherein said stream is either in a liquid or in a vapour phase, in the presence of a heterogeneous acid catalyst, to get a final solution of (L)-lactic acid in acetic acid, wherein the water is almost completely separated from the final solution;
   a) carrying out an acetylation of said (L)-lactic acid in said acetic acid with acetic anhydride to give (S)-2-acetyloxypropionic acid in acetic acid;
   b) isolating said (S)-2-acetyloxypropionic acid by distilling off acetic acid and excess acetic anhydride from the (S)-2-acetyloxypropionic acid;
   c) chlorinating said (S)-2-acetyloxypropionic acid with thionyl chloride to give (S)-2-acetyloxypropionyl chloride; and
   d) purifying said (S)-2-acetyloxypropionyl chloride.

7. The process according to claim 6, wherein said heterogeneous acid catalyst is selected from the group consisting of: a sulfonic acid resin, a zeolite and a montmorillonite.

8. The process according to claim 6, wherein the acetylation of step a) is carried out in a distillation column.

9. The process according to claim 6, wherein the distilled acetic acid is recycled into the aqueous (L)-lactic acid solution in step a').

10. The process according to claim 6, wherein said chlorination is carried out in a series of at least 2 reactors, wherein each reactor is equipped with its own condensation unit to condense unreacted $SOCl_2$, and wherein the condensed $SOCl_2$ is recycled back to the starting chlorination reactor.

11. The process according to claim 6, wherein the purifying of said (S)-2-acetyloxypropionyl chloride is done by distillation.

12. The process according to claim 1, wherein the concentration of (L)-lactic acid in acetic acid is from 20% to 60% by weight.

13. The process according to claim 1, wherein the concentration of (L)-lactic acid in acetic acid is from 40% to 60% by weight.

14. The process according to claim 6, wherein the concentration of (L)-lactic acid in acetic acid is from 20% to 60% by weight.

15. The process according to claim 6, wherein the concentration of (L)-lactic acid in acetic acid is from 40% to 60% by weight.

16. A continuous process for the preparation of (S)-2-acetyloxypropionic chloride starting from a commercial grade aqueous (L)-lactic acid solution comprising the following steps:
   a') replacing water with acetic acid in said aqueous (L)-lactic acid solution by distilling off water from the aqueous (L)-lactic acid solution while simultaneously introducing an acetic acid stream, wherein said stream is either in a liquid or in a vapour phase, to get a final solution of (L)-lactic acid in acetic acid, wherein the water is almost completely separated from the final solution,
   a) carrying out an acetylation of said (L)-lactic acid in said acetic acid with acetic anhydride to give (S)-2-acetyloxypropionic acid in acetic acid;
   b) recovering the (S)-2-acetyloxypropionic acid by distilling off acetic acid and excess anhydride from (S)-2-acetyloxypropionic acid;
   c) chlorinating said (S)-2-acetyloxypropionic acid with thionyl chloride to give (S)-2-acetyloxypropionyl chloride; and
   d) purifying said (S)-2-acetyloxypropionyl chloride.

17. The process according to claim 16, wherein the acetylation of step a) is carried out in a distillation column.

18. The process according to claim 16, wherein step a') is carried out in a distillation column and wherein the acetic acid distilled off in step b) is recycled to the acetic acid stream entering the distillation column.

19. The process according to claim 18, wherein said chlorination is carried out in a series of at least 2 reactors, wherein each reactor is equipped with its own condensation unit to condense unreacted $SOCl_2$, and wherein the condensed $SOCl_2$ is recycled back to the starting chlorination reactor.

20. The process according to claim 16, wherein the concentration of (L)-lactic acid in acetic acid is from 20% to 60% by weight.

21. The process according to claim 16, wherein the concentration of (L)-lactic acid in acetic acid is from 40% to 60% by weight.

22. The process according to claim 1, wherein the concentration of water in the final solution is less than 3% by weight.

23. The process according to claim 6, wherein the concentration of water in the final solution is less than 3% by weight.

24. The process according to claim 16, wherein the concentration of water in the final solution is less than 3% by weight.

* * * * *